United States Patent [19]

Sakakibara et al.

[11] Patent Number: 4,835,308

[45] Date of Patent: May 30, 1989

[54] PROCESS FOR PRODUCING TRIMELLITIC ACID

[75] Inventors: Yasuzo Sakakibara, Kudamatsu; Ken-ichi Ueda, Tokuyama; Kouji Tomita, Tokuyama, all of Japan

[73] Assignee: Idemitsu Petrochemical Co., Ltd., Tokyo, Japan

[21] Appl. No.: 93,215

[22] Filed: Sep. 4, 1987

[30] Foreign Application Priority Data

Sep. 9, 1986 [JP] Japan .................................. 61-210712

[51] Int. Cl.$^4$ ............................................ C07C 51/265
[52] U.S. Cl. ...................................... 562/413; 562/416
[58] Field of Search ................................. 562/413, 416

[56] References Cited

U.S. PATENT DOCUMENTS 3,683,016 8/1972 Darin .................................... 562/413
4,398,040 8/1983 Suzuki .................................. 562/413

Primary Examiner—Michael L. Shippen
Attorney, Agent, or Firm—Antonelli, Terry & Wands

[57] ABSTRACT

A process for producing trimellitic acid by oxidizing pseudocumene with a molecular oxygen-containing gas in an acetic acid solvent in the presence of a catalyst comprising one or more cobalt compounds, one or more manganese compounds, and one or more bromine compounds, wherein the total amount of the cobalt compound is in the range of 0.01–1.0% by weight of the acetic acid solvent based on the weight of cobalt metal, the total amount of the manganese compound is in the range of 0.01–0.1% by weight of the acetic acid solvent based on the weight of manganese metal, the total amount of the bromine compound is in the range of 0.01–2.0% by weight of the acetic acid solvent based on the weight of bromine atoms, with the proviso that the atomic ratio of bromine to cobalt and manganese [Br/(Co+Mn)] is in the range of 2.51–2.99, which process comprises at least two reaction-stages comprising the preceding reaction-stage in which the reaction temperature is maintained in the range of 110° to 180° C. and the succeeding reaction-stage in which the reaction temperature is maintained in the range of 180°–230° C., the whole amounts of the cobalt compound, the manganese compound, the bromine compound, the acetic acid solvent and the reactant being introduced into the first stage of the preceding reaction-stage and the oxidation reaction being virtually completed in the succeeding reaction-stage.

12 Claims, No Drawings

PROCESS FOR PRODUCING TRIMELLITIC ACID

BACKGROUND OF THE INVENTION

1. Field of the Invention

The present invention relates to a process for producing trimellitic acid which can be suitably used as a raw material for plasticizers, polymers having a heat-resisting property, etc., by the oxidation of pseudocumene with a molecular oxygen-containing gas.

2. Description of the Prior Art

Trimellitic acid is a useful compound as a rwa material for thermostable plasticizers or various heat-resistant polymers, so that the development of an effective process by which trimellitic acid having a sufficiently high purity can be prepared at a low cost has been required.

It has previously been known that there are some methods for preparing trimellitic acid by oxidizing pseudocumene with a gas containing molecular oxygen in an acetic acid solvent in the presence of a catalyst comprised of one or more heavy metal compounds and one or more bromine compounds; and the methods characterized by continuously conducting the oxidation are described in for example, Japanese Patent Publication No. 23732/70, Japanese Patent Laid-open Nos. 7173/71, 2932/81, 167942/82, Japanese Patent Publication No. 5898/83, etc..

Although each of these methods has an advantage that the product having a moderately good quality can be continuously obtained, every method is not yet very sufficient in the practical use.

That is to say, the method described in Japanese Patent Laid-open No. 7173/71 is not only a complicated process characterized by conducting the oxidation with multi-stage operations by changing the composition of the quarternary catalyst comprising cobalt, manganese, cerium and bromine from one stage to another, but also an uneconomical process because the recycling of the catalyst which is very expensive is practically impossible by the necessity that the composition of the catalyst has to be adjusted in each stage.

The method described in Japanese Patent Laid-open No. 23732/70 is a multi-stage oxidation process characterized in that the oxidation is successively conducted by introducing cobalt and bromine compounds into the first stage and by adding one or more manganese compounds to the reaction system in the second stage, and the method described in Japanese Patent Laid-open No. 167942/82 is a multi-stage oxidation process characterized in that the reaction in the first stage is conducted by introducing the whole amounts of one or more cobalt compounds and one or more bromine compounds, and a part of one or more manganese compounds until the concentration of the unreacted pseudocumene in the liquid product for the first stage is less than 0.4% by weight, and the oxidation is then completed in the second stage by adding the other part of one or more manganese compounds to the reaction system to re-adjust the composition of the catalyst.

These methods, however, have a disadvantage that the yield of and the selectivity for trimellitic acid are not suffciently high since the oxidation of pseudocumene to carbon dioxide and water, which is the most undesired side reaction for the selective oxidation of pseudocumene to trimellitic acid, is relatively significant because these methods are designed actually for improving the effectiveness of the second stage oxidation by the addition of one or more manganese compounds, and the composition of the catalyst used in the first stage oxidation is, therefore, not sufficiently suitable for the selective oxidation.

The method described in Japanese Patent Laid-open No. 167942/82 has such a risk that the product is contaminated with bromine since a large amount of bromine is used as a catalyst component in the method.

Moreover, these methods have the disadvantages that the operation is complicated and the recycling of the used catalyst is practically difficult because it is necessary to change and limit the composition of the catalyst in each stage.

The method described in Japanese Patent Publication No. 5898/83 is a continuously-flow oxidation process by double-stage operations characterized in that the first stage oxidation is conducted at 110°–170° C. to obtain the first-stage reaction product in which the concentration of pseudocumene is not more than 10% by weight, which is succeeded by second stage oxidation at 180°–240° C. However, this method has a disadvantage that the activity of the catalyst used and the selectivity for trimellitic acid are not practically sufficient; consequently, the yield of trimellitic acid is low because the composition of the catalyst used, in particularly the ratio of bromine to cobalt and manganese, is not kept at a ratio in a suitable range for the desired oxidation, although the problem of the difficulty in recycling the used catalyst can be removed by using the operation that the whole quantity of the catalyst components is charged in the first stage of the reaction.

SUMMARY OF THE INVENTION

It is an object of the present invention to provide an excellent process industrially producing for trimellitic acid by the oxidation of pseudocumene with a gas containing molecular oxygen, said method having the following advantages: the advantages described above can be removed; the reaction can be conducted by simple operations; the recycling of the used catalyst can be easily operated; and both the high catalytic activity and the high selectivity for trimellitic acid can be attained with the depression of the so-called complete oxidation that produces carbon dioxide and water, and the remarkable enhancement in the yield of trimellitic acid can consequently be achieved.

As the results of our extensive study to remove the above disadvantages, we have found that the object of the present invention can easily be achieved by conducting the oxidation with multi-stage operations, by employing at least two reaction-stages of which temperatures are different from each other by introducing the whole amounts of all of the catalyst-components into the first stage of the reaction and keeping the composition of the catalyst in a specified range, and we have established the present invention on the basis of the finding.

That is, the present invention provides a process for producing trimellitic acid by oxidizing pseudocumene with an molecular oxygen-containing gas in an acetic acid solvent in the presence of a catalyst comprising one or more cobalt compounds, one or more manganese compounds, and one or more bromine compounds, wherein the the total amount of the cobalt compound is in the range of 0.01–1.0% by weight of the acetic acid solvent based on the weight of cobalt metal, the total amount of the manganese compound is in the range of 0.01–1.0% by weight of the acetic acid solvent based on the weight of manganese metal, the total amount of the bromine compound is in the range of 0.01–2.0% by weight of the acetic acid solvent based on the weight of bromine atoms, with the proviso that the atomic ratio of bromine to cobalt and manganese [Br/(Co+Mn)] is kept in the range of 2.51–2.99, which process comprises at least two reaction-stages comprising the preceding reaction-stage in which the reaction temperature is maintained in the range of 110° to 180° C. and the succeeding reaction-stage in which the reaction temperature is maintained in the range of 180°–230° C., the whole amounts of the cobalt compound, the manganese compound, the bromine compound, the acetic acid solvent, and the reactant being introduced into the first stage of the preceding reaction-stage and the oxidation reaction being virtually completing in the succeeding reaction-stage.

DETAILED DESCRIPTION OF THE INVENTION

The present invention is described more precisely below.

According to the present invention, pseudocumene (1,2,4-trimethylbenzene) is oxidized to trimellitic acid (1,2,4-benzenetricarboxylic acid) with a molecular oxygen-containing gas in an acetic acid solvent in the presence of the oxidation catalyst, by means of multi-stage or multi-step operations by using at least two reaction-stages comprising the preceding reaction-stage and the succeeding reaction-stage whose temperature ranges are different from each other; by introducing the whole amount of the catalyst to be used, the whole amount of the acetic acid solvent to be used, the whole amount of pseudocumene to be used, and molecular oxygen-containing gas into the first stage of the reaction (the first reaction-stage of the preceding reaction-stage) to initiate the oxidation at the first stage; and the preceding stage oxidation is, thus, initiated and continued.

After the conversion of pseudocumene became sufficiently high, namely, as high as preferably not less than 40%, more preferably not less than 50% in the preceding rection-stage, the temperature of the resulting liquid reaction mixture is elevated and maintained at a temperature in the prescribed range for the oxidation of the succeeding stage, or the resulting liquid reaction mixture is transferred into another reaction region in which temperature has already been maintained at a prescribed temperature of the oxidation of the succeeding stage, and the the oxidation of the succeeding stage is then carried out until the oxidation is virtually completed.

The amount of acetic acid as a solvent can be double or more, preferably from 4 to 10 times, by weight, of the weight of pseudocumene. Acetic acid which contains water in concentration of not more than 20% by weight can also be used.

The oxidation catalysts which can be employed are the catalysts comprising cobalt, manganese, and bromine, and these components of the catalysts can be added to the reaction system as the following compounds. That is, both cobalt compound which is soluble in acetic acid and manganese compound which is soluble in acetic acid can be employed, and suitable forms of cobalt and / or manganese can be, for example, the salts of organic acids such as acetates, propionates, naphthenates, octenates, etc.; hydroxides; halides such as chlorides, bromides, etc.; the salts of inorganic acids such as borates, nitrates, carbonates, etc.; organic complexes such as acetylacetonates, carbonyls, ammine complexes, oxocomplexes, etc.; and the likes. Especially preferable forms of cobalt or manganese are the acetates, carbonates, hydroxides, bromides, etc.

Some illustrative examples of the bromine compounds which can be employed are bromine; hydrogen bromide; ammonium bromide; alkaline metal bromides such as sodium bromide, lithium bromide, potassium bromide, cesium bromide, etc.; other inorganic bromine compounds such as cobalt bromide, manganese bromide, cerium bromide, etc.; and organic bromine compounds such as tetrabromoethane, bromoacetic acid, benzyl bromide, etc.. The preferred bromine compounds are sodium bromide, cobalt bromide, manganese bromide, ammonium bromide, and sodium bromide is especially preferable.

One or more cobalt compounds, one or more manganese compounds, and one or more bromine compounds can be selected from the corresponding compounds described above and used.

The total amount of the cobalt compound has to be kept in the range of 0.01–1.0% by weight of the acetic acid solvent based on cobalt metal. If the amount of the cobalt catalyst is less than 0.01 wt % (as cobalt metal) the rection rate will significantly decrease, and on the other hand, if it is more than 1.0 wt % (as cobalt metal) the amount of the cobalt salt of trimellitic acid will be no longer negligible, and consequently the yield of the desired product will decrease.

The total amount of the manganese compound has to be kept in the range of 0.01–1.0% by weight of the acetic acid solvent based on the weight of manganese metal. If the amount of the manganese catalyst is less than 0.01 wt % (as manganese metal), a sufficiently high catalytic activity cannot be attained, or the yield of carbon dioxide will increase. On the other hand, if it is less than 1.0 wt % (as manganese metal), the yield of the desired product will decrease.

An especially preferred ratio of the total amount of the cobalt compound to that of the manganese compound to attain the high catalytic activity, the high selectivity, and easy operation in recovering the used catalyst is in the range of usually 5:1–1:10, preferably 4:1–1:4 by atomic ratio of cobalt metal to manganese metal (Co:Mn).

The total amount of the bromine compound has to be kept in the range of 0.01–2.0% by weight of the acetic acid solvent based on the weight of bromine atom, and at the same time, in the range of 2.51–2.99, preferably 2.6–2.9 by atomic ratio of bromine to cobalt and manganese (Br/CO+Mn). If the total amount of the bromine catalyst is less than 2.51 by the atomic ratio described above, the activity of the catalyst obtained will not be sufficiently high. On the other hand, if the ratio is more than 2.99, the concentration of bromine-components in the product will be unneggligible, and as a result, the cost for the purification of the product will usually increase, the cost of the catalyst may increase, and the effectiveness in the recovery of the used catalyst may in some cases decrease, although the catalytic activity usually incrases.

One of the important points in the present invention is that the oxidation is initiated by bringing molecular oxygen-containing gas into contact with a mixture comprising the whole amount of one or more cobalt compounds, the whole amount of one or more manganese compounds, the whole amount of one or more bromine compounds, the whole amount of the acetic acid solvent, and the whole amount of pseudocumene at a temperature in the prescribed range. That is, the oxidation has to be initiated and conducted by introducing the whole amounts of the catalyst, the solvent, and pseudocumene into the initial stage of the preceding reaction-stage. If a part of or the whole of the catalyst-components such as the manganese compound, etc. is introduced into the reaction-stages after the preceiding reaction-stage, the undesired complete oxidations to carbon dioxide, carbon monoxide and water may increase and, on the other hand, the yield of trimellitic acid will decrease, and operations for the reaction will be complicated. Therefore, it is not preferred to employ such manners.

A suitable molecular oxygen-containing gas used as the oxidant is usually air, and pure oxygen or exhaust gas from industries is also suitably employed. The molecular oxygen-containing gas such as air, etc. is usually fed continuously into the liquid reactant or reaction mixture through one or more gas inlets of the reactor and, in the case that the reaction is conducted by multistage operations in two or more reactors connected in series, a manner in which the gas containing oxygen molecules is continuously introduced by controlling its feed-rate into each reactor through one or more gas inlets of each reactor is usually employed, as will be described below.

The reaction temperature for ht erection of the preceding stage has to be maintained at a temperature in the range of 110°–180° C., preferably 120°–170° C., and that for the reaction of the succeeding stage at a temperature in the range of 180°–230° C., preferably 190°–220° C. If the reaction temperature of the reaction of the preceding stage reaction is lower than 110° C., the reaction rate may extremely be low; and if it is higher than 180° C., undesired reactions such as the complete oxidation, etc. will increase, and the deactivation of the catalyst may often occur. Therefore, such operations produce some disadvantages. On the other hand, if the reaction temperature for the reaction of the succeeding stage is lower than 180° C. it will be difficult to complete the oxidation to trimellitic acid; and if it is higher than 230° C., the decompositions of the solvent and the reactants to carbon dioxide will increase, and other by-products such as colored impurities also increase. Therefore, both operations are disadvantageous.

The reaction pressure has to be maintained in the range in which the acetic acid solvent can be kept to be a liquid phase at the reaction temperature employed, preferably in the range of 4–50 kg/cm$^2$. With respect to the partial pressure of oxygen over the reaction system, it is preferred to control the feed rate of the molecular oxygen-containing gas into the reactor to keep the concentration of oxygen in the exhaust gas out of the reactor to be in the range of 1–8% by volume.

According to the present invention, the intended oxidation is virtually completed by conducting the reaction of the succeeding reaction after the reaction of the preceding stage was accomplished as described above, and, as far as the reaction is conducted by the method described above, it is possible to employ a variety of reaction techniques. For example, the reaction can be completed by means of a double-stage operation by employing one single-stage reaction for the preceding reaction-stage and the other single-stage reaction for the succeeding reaction-stage, or either reaction-stage can be further divided into sub-stages, and the reaction can be then conducted by multi-stage operation with three or more reaction-stage. Moreover, all the reaction-stages can be conducted in the same single reaction-region or reactor, or a part of or all of the reaction-stages can be conducted in the different reaction-regions and/or reactors. In the case that two or more reaction-stages are conducted in the same single reaction-region or reactor the reaction can be conducted by suitably changing the reaction temperature from one stage to another with the reaction time. On the other hand, in the case of using two or more reaction-regions and/or reactors, the reaction can be conducted by flowing continuously or intermittently the liquid reaction mixture through a series of reaction-regions and/or reactors in which temperatures are maintained at the respective prescribed temperatures. As mentioned above, both batchwise multistage operations and continuously-flow multistage operations can preferably be employed as the reaction techniques in the present invention.

Trimellitic acid which is produced by means of the present invention can be isolated and purified by a variety of known techniques.

According to the present invention, the amount of carbon dioxide generated in the course of the complete oxidation reaction, degradation reaction, etc. can be decrased, and trimellitic acid of high purity can be produces easily in high yield. Therefore, the industrial value of the invention is extremely large.

EXAMPLES AND COMPARATIVE EXAMPLES

The present invention is illustrated in more details by the following examples. However, these examples are not to be construed to limit the scope of the invention.

EXAMPLE 1 and 2, and COMPARATIVE EXAMPLES 1 and 2

A 1-l autoclave with titanium lining equipped with a reflux condenser, a stirrer having rotary blades, and a nozzle for air-blowing was used for rections. After a liquid rectant mixture, a solvent and a catalyst were charged to the reactor and the temperature was elevated, the reaction was initiated by introducing subsurface air into the resulting solution. Oxygen in the exhaust gas leaving off from the reactor was quantitatively analyzed by means of an oxygen-meter, and carbon dioxide in the exhaust gas was trapped with an alkaline solution and the resulting solution was quantitavely analyzed to determine the yield of carbon dioxide. After the reaction was completed, the reaction products were taken out of the reactor, and the reaction products (acids) were converted to the corresponding methyl esters by esterification, and then the resulting methyl esters were quantitatively analyzed by gas-chromatography.

In Example 1 and 2 and Comparative example 1, the reaction was initiated after the whole amount of each catalyst-component was previously charged to the reaction system. On the other hand, in Comparative example 2, the reaction was initiated after all of the catalyst-components except for manganese was charged to the reaction system, and after the reaction was continued for 40 minutes, a manganese compound was added to the reaction system.

The amounts of the catalyst-components, the solvent, the other raw materials for the reaction, also the reaction conditions employed were shown in Table 1 with the results.

EXAMPLE 3, and COMPARATIVE EXAMPLES 3 and 4

By using gas-liquid-contact-type reaction apparatus comprising three titanium tubular reactors each of which has an inside diameter of 70.3 mm, a length of 2500 mm, and a nozzle for gas-blowing inside the reactor, the continuously flow reactions were independently conducted under the respective reaction conditions shown in Table 1.

In both Example 3 and Comparative example 3, the whole amounts of the prescribed catalyst-components to be charged, acetic acid, and pseudocumene were continuously introduced into the first reactor. On the other hand, in comparative example 4, the manganese compound was introduced into the outlet of the first reactor.

Suitable quantities of the liquid reaction mixtures were occasionally withdrawn out of the outlet of the respective reactors and quantitatively analyzed by the same technique as employed in Example 1. The results were shown in Table 1.

In Table 1 were shown the results for the liquid products taken out of the first reactor in the cases of the continuously flow reactions. The reaction temperature, the reaction pressure, and the reaction time were kept at 190° C., 20 kg/cm$^2$, and 60 min. in the second reactor, and 210° C., 30 kg/cm$^2$, 60 mom. in the third reaction.

The reaction ws completed in the third reactor, and the oxidation ratio of pseudocumene was 99.1% while the purity of trimellitic acid obtained was 97% in Example 3. In Comparative Examples 3 and 4, on the other hand, the evolutions of carbon dioxide were significantly high and the final yield of the desired products were low. The amount of carbon dioxide evolved in the continuously flown reaction means the concentration of carbon dioxide in the exhaust gas out of the third reactor.

In addition, when the procedure of Example 1 was exactly repeated except that the atomic ratio of Br/(Co+Mn) was kept at which means that 3,4 (The amount of bromine used was increased), trimellitic acid contaminated with 1,000 ppm of bromine was obtained.

TABLE 1

| | | Type of reaction operation employed | | | | | | | |
|---|---|---|---|---|---|---|---|---|---|
| | | Batch operation | | | | | Continuously flow method | | |
| Composition of the reaction mixture charged and Reaction condition | Units | Example 1 | Example 2 | Comparative Example 1 | Comparative Example 2 | Units | Example 3 | Comparative Example 3 | Comparative Example 4 |
| Amount of pseudocumenne charged | g | 48.1 | 48.1 | 48.1 | 48.1 | g/Hr | 1,000 | 1,000 | 1,000 |
| Acetic acid | g | g.a.a. | g.a.a. | g.a.a. | g.a.a. | | a.a.a. | a.a.a. | a.a.a. |
| Amount of acetic acid charged | g | 192 | 192 | 192 | 192 | g/Hr | 4,000 | 4,000 | 4,000 |
| Amount of cobalt acetate charged | g | 0.81 | 1.06 | 0.81 | 0.81 | g/Hr | 16.91 | 16.91 | 16.91 |
| Amount of cobalt bromide charged | g | | | | | g/Hr | | | |
| Cobalt/Acetic acid | wt % | 0.10 | 0.10 | 0.1 | 0.1 | wt % | 0.1 | 0.1 | 0.1 |
| Amount of manganese acetate charged | g | 0.40 | | 0.40 | (0.40) | g/Hr | 8.92 | 8.92 | (8.92) |
| Amount of manganese bromide | g | | 0.47 | | | g/Hr | | | |
| Manganese/Acetic acid | wt % | 0.05 | 0.05 | 0.05 | (0.05) | wt % | 0.05 | 0.05 | (0.05) |
| Amount of sodium bromide charged | | 1.38 | 0.35 | 0.99 | 1.38 | g/Hr | 28.9 | 21.5 | 28.9 |
| Bromine/Acetic acid | wt % | 0.56 | 0.55 | 0.40 | 0.56 | wt % | 0.56 | 0.4 | 0.56 |
| Catalyst charged to the preceding stage | — | Co—Mn—Br | Co—Mn—Br | Co—Mn—Br | Co—Br—(Mn)* | — | Co—Mn—Br | Co—Mn—Br | Co—Br—(Mn)** |
| Br/(Co + Mn)   Atomic ratios | | 2.7 | 2.7 | 2.0 | 2.7 | | 2.7 | 2.0 | 2.7 |
| Reaction temperature | °C. | 140,215 | 140,215 | 140,215 | 140,215 | °C. | 160 | 160 | 160 |
| pressure | kg/cm² G | 20 | 20 | 20 | 20 | kg/cm² G | 20 | 20 | 20 |
| Flow rate of exhaust gas | l/Hr | 140 | 140 | 140 | 140 | l/Hr | 2,000 | 2,000 | 2,000 |
| Reaction time | min | 80,100 | 80,100 | 80,100 | 80,100 | min | 60 | 60 | 60 |
| Reaction products | | | | | | | | | |
| Phthalic acid | wt % | 0.4 | 0.3 | 0.6 | 1.0 | wt % | 1.7 | 1.9 | 2.9 |
| Dimethyl benzene carboxylic acid | wt % | 0.0 | 0.0 | 0.0 | 0.0 | wt % | 41.7 | 43.6 | 49.7 |
| Methylphthalic acid | wt % | 3.0 | 2.9 | 3.0 | 2.8 | wt % | 50.4 | 50.6 | 45.6 |
| Trimellitic acid | wt % | 96.6 | 96.8 | 96.4 | 96.2 | wt % | 6.2 | 3.9 | 1.8 |
| Heavy fraction | g | 5.8 | 5.9 | 5.6 | 5.7 | | | | |
| Amount of carbon dioxide evolved | mol | 0.13 | 0.14 | 0.16 | 0.19 | mol | 2.3 | 3.0 | 3.8 |
| Yield of trimellitic acid | mol % | 91.5 | 91.4 | 88.7 | 86.2 | | | | | g.a.a.: glacial acetic acid,
a.a.a.: 90% aqueous solution of acetic acid,
*further added 40 minutes after,
**added at the outlet of the first reactor

What is claimed is:

1. A process for producing trimellitic acid by oxidizing pseudocumene with a molecular oxygen-containing gas in an acetic acid solvent in the presence of a catalyst comprising one or more cobalt compounds, one or more manganese compounds, and sodium bromide, wherein the total amount of the cobalt compound is in the range of 0.01–1.0% by weight of the acetic acid solvent based on the weight of cobalt metal, the total amount of the manganese compound is in the range of 0.01–1.0% by weight of the acetic acid solvent based on the weight of manganese metal, the amount of sodium bromide is in the range of 0.01–2.0% by weight of the acetic acid solvent based on the weight of bromine atoms, with the proviso that the atomic ratio of bromine to cobalt and manganese [Br/(Co+Mn)] is in the range of 2.60–2.99, which process comprises at least two reaction-stages comprising a preceding reactionstage in which the reaction temperature is maintained in the range of 110°–180° C. and a succeeding reaction-stage in which the reaction-stage temperature is maintained in the range of 180°–230° C., the whole amounts of the cobalt compound, the manganese compound, sodium bromide, the acetic acid solvent and the reactant being introduced into the first stage of the preceding reaction-stage and the oxidation reaction being virtually completed in the succeeding reaction-stage.

2. A process according to claim 1, wherein the cobalt compound is cobalt acetate or cobalt bromide.

3. A process according to claim 1, wherein the manganese compound is manganese acetate or manganese bromide.

4. A process according to claim 1, wherein the cobalt compound is cobalt acetate or cobalt bromide, and manganese compound is manganese acetate or manganese bromide.

5. A process according to claim 1, wherein the atomic ratio of the cobalt to manganese is 4:1–1:4.

6. A process according to claim 1, wherein the reaction temperature is maintained in the range of 120°–180° C. at the preceding reaction-stage, and is maintained in the range of 190°–220° C. at the succeeding reaction-stage.

7. A process according to claim 1, wherein the oxidation rection is carried out at the proceeding reaction-stage until the conversion of pseudocumene become not less than 50%.

8. A process according to claim 1, wherein the molecular oxygen-containing gas is air.

9. A process according to claim 1, wherein the reaction pressure is 4–50 kg/cm$^2$.

10. A process according to claim 8, wherein the oxidation reaction is carried out at the preceding reaction-stage until the conversion of pseudocumene becomes not less than 50%.

11. A process according to claim 6, wherein the oxidation reaction is carried out at the preceding reaction-stage until the conversion of pseudocumene becomes not less than 50%.

12. A process according to claim 7, wherein the atomic ratio of the cobalt to manganese is 4:1–1:4.

* * * * *